United States Patent [19]

Rohwedder et al.

[11] Patent Number: 5,419,327
[45] Date of Patent: May 30, 1995

[54] ACOUSTIC THERAPY MEANS

[75] Inventors: Arnim Rohwedder, Fuerth; Sylvester Oppelt, Memmelsdorf, both of Germany

[73] Assignee: Siemens Aktiengesellschaft, Munich, Germany

[21] Appl. No.: 154,552

[22] Filed: Nov. 19, 1993

[30] Foreign Application Priority Data

Dec. 7, 1992 [DE] Germany ............... 42 41 161.0

[51] Int. Cl.6 ........................... A61B 17/22
[52] U.S. Cl. ......................... 128/660.03; 601/4
[58] Field of Search ............ 128/660.01, 660.03, 128/660.07, 65.31; 601/1–4

[56] References Cited

U.S. PATENT DOCUMENTS

| | | | |
|---|---|---|---|
| 4,674,505 | 6/1987 | Pauli et al. | |
| 4,962,754 | 10/1990 | Okazaki | 601/4 |
| 5,054,469 | 10/1991 | Ishida | 601/4 |
| 5,072,722 | 12/1991 | Granz | 601/4 |
| 5,158,085 | 10/1992 | Belikan et al. | 601/4 |
| 5,174,294 | 12/1992 | Saito et al. | 601/4 |
| 5,213,102 | 5/1993 | Kudo et al. | 601/2 |
| 5,269,292 | 12/1993 | Granz et al. | |

FOREIGN PATENT DOCUMENTS

| | | | |
|---|---|---|---|
| 0168559 | 1/1986 | European Pat. Off. | |
| 0265742 | 5/1988 | European Pat. Off. | 601/4 |
| 0244730 | 7/1990 | European Pat. Off. | |
| 0511506 | 11/1992 | European Pat. Off. | 601/4 |
| 3146628 | 1/1985 | Germany | |
| 3900893 | 8/1989 | Germany | |

*Primary Examiner*—Krista M. Pfaffle
*Attorney, Agent, or Firm*—Hill, Steadman & Simpson

[57] ABSTRACT

A therapy system for treatment of a subject with focused acoustic waves has a source of focused acoustic waves, equipment for displacing the focus none of the focused acoustic waves and the subject to be treated relative to one another, and a locating system which non-invasively acquires the three-dimensional spatial position of a region within the subject to be charged with the focused acoustic waves relative to the focus zone of the focused acoustic waves continuously as a function of time. The system further includes a display which graphically displays the three-dimensional data generated by the locating system.

35 Claims, 6 Drawing Sheets

ACOUSTIC THERAPY MEANS

BACKGROUND OF THE INVENTION

1. Field of the Invention

The present invention is directed to a therapy system for treating a subject with focused acoustic waves, of the type having a source of focused acoustic waves, means for causing relative displacement of the focus zone of the focused acoustic waves and the subject to be treated, and a locating means for locating a region within the subject to be charged with the focused acoustic waves.

2. Description of the Prior Art

Therapy systems of the above general type, which advantageously operate non-invasively, are employed, for example, for the disintegration of calculi (lithotripsy), for the treatment of tumor pathologies (hyperthermia) or for treating bone conditions (osteorestoration). For implementing a therapy, the position of the region to be charged with the acoustic waves is first determined with the locating means. Subsequently, the focus zone of the acoustic waves and the subject to be treated are displaced relative to one another such that the focus zone coincides with the region to be charged with acoustic waves. This region is then charged with acoustic waves in the required way by the source of acoustic waves.

The problem arises in practice that the region to be charged with acoustic waves is not at rest, but exhibits a movement even given a sedate patient, this movement being caused, among other things, by the respiration of the patient. According to a method disclosed by German Patent 31 46 628, in order to improve the "on target" reliability, the emission of shockwaves is only allowed to ensue in such a phase of the respiratory cycle wherein the region to be charged with acoustic waves moves little. Another improvement of the "on target" reliability can be achieved when, according to European Application 0 244 730, a chronological correlation of the operation of the locating means such as an x-ray system, and the output of the acoustic waves is additionally produced. Because, however, the movement of the region to be charged with the acoustic waves is subject to certain irregularities, an adequately high "on target" reliability can not be achieved under all circumstances even with this latter method. This also true of a therapy apparatus disclosed by German OS 39 00 893 wherein the overlap between a calculus to be disintegrated and the focal zone is calculated and is displayed as a function of time, so that the operating personnel have additional information available.

Moreover, German OS 40 34 533 discloses the use of an ultrasound locating means, operating according to the echo locating principle.

A therapy system disclosed by European Application 0 168 559 also offers an improvement in the targeting reliability, by using two locating devices spatially correlated to one another, either both operating on an ultrasound basis or one operating on an ultrasound basis and the other operating on an x-ray basis. Since only two slices of the patient can be scanned in the case of two locating means operating on an ultrasound basis, the position of the region can no longer be identified as soon as the region to be charged with the acoustic waves moves out of one of the two slices. This is similarly true for the combined x-ray and ultrasound locating. Although the region will usually be visible in the x-ray image, the region will repeatedly enter and leave the slice scanned with the ultrasound. The result is that the spatial position of the region cannot be identified. Again, therefore, the "on target" reliability is in need of improvement.

SUMMARY OF THE INVENTION

It is an object of the present invention to provide a therapy system of the type initially described with an improved locating device, and to fashion this therapy system such that the prerequisites for a high "on target" reliability are established.

This object is achieved in a therapy system for treatment with focused acoustic waves in accordance with the principles of the present invention, having a source of focused acoustic waves, means for displacing the focus zone of the focused acoustic waves and a subject to be treated relative to one another, and a locating means which non-invasively acquires the spatial position of a region within the subject to be charged with the focused acoustic waves as a function of the time. In the therapy system of the invention, thus, the spatial position of the region to be charged with the acoustic waves is not only acquired at specific, discrete points in time separated from one another by greater time intervals, for example once during a respiratory cycle, but is continuously acquired, i.e. in real time. Known specific locating devices, particularly locating devices operating conventionally on an acoustic basis, do not allow a continuous acquisition of the spatial position of the region to be charged with acoustic waves in the strictest sense of the word continuous used herein. In the therapy system of the invention, the acquisition of the spatial position should ensue with a repetition rate that is high (at least twenty times higher) in comparison to the frequency with which the region moves, or the acquisition of the spatial position of the region should ensue at time intervals that do not significantly exceed a few hundredths of a second, for example 0.25 seconds. The repetition rate with which the acquisition of the spatial position ensues should also be dimensioned such that the distance traversed by the region to be charged with the acoustic waves between two successive acquisitions of the spatial position lies at most on the order of magnitude of the dimensions of the region to be charged with the acoustic waves. In comparison to the known systems, the locating means of the therapy device of the invention thus offers substantially more decisive information with resect to the position of the region to be charged with the acoustic waves, in that the spatial position of the region is known at practically all times. The prerequisite for a high "on target" reliability is thus also created, since it is critical therefor to constantly have information with respect to the current position of the region available. At the same time, the advantage is achieved that the emission of acoustic waves can ensue not only at specific, discrete points in time, but can essentially occur at arbitrary points in time.

In a preferred embodiment of the invention the means for displacement cause the positioning of the focus zone to be synchronized with the region to be charged with the focused acoustic waves, on the basis of the data supplied by the locating means. An extremely high "on target" reliability is achieved in this case, coming close to the ideal except for slight deviations. The slight deviations are caused in that the synchronization of the focus zone does not ensue precisely synchronously, but lags behind the region to be charged with the focused acoustic waves in accord with the time constant which is inherently associated with the means for displacement are affected.

In another preferred embodiment of the invention, control and measuring means are provided which, on the basis of the data supplied by the locating means, predetermine the location of the region to be charged with the focused acoustic waves. There is then the possibility of eliminating the time constant of the means for displacement. The deviations from the maximally possible "on target" reliability are slight, since the errors that can occur in the predetermination of the location of the region are only slight. The control and measuring means, moreover, preferably contain fuzzy logic.

There is also the possibility of charging the region with the focused acoustic waves only when the predetermined position thereof coincides with the focus zone. Even when a synchronization of the focus zone does not ensue, one can still achieve a high "on target" reliability since the source of acoustic waves—taking the propagation time of the acoustic waves to the region to be charged into consideration—is activated to emit acoustic waves at a point in time such that the acoustic waves arrive in the focus zone at the slightly later point in time at which the predetermined location of the region to be charged coincides with the focus zone.

In another embodiment of the invention, the control and measurement means based on the data supplied by the locating means and taking the geometry of the focus zone into consideration—identify an alignment of the focus zone and the object to be treated relative to one another, and an enhanced dwell probability of the region to be charged with the focused acoustic waves in the focus zone is achieved. Since the focus zone is a three-dimensional, usually cigar-shaped structure in practice, the control and measurement means can find an alignment of the source relative to the subject to be treated on the basis of the movement executed by the region to be charged with the focused acoustic waves, in which alignment it is most likely that the region to be charged with the focused acoustic waves stays an optimally long time in the focus zone, i.e., the dwell probability is enhanced. To the extent anatomical reasons do not prohibit a particular alignment, there is then the possibility of aligning the source and the subject relative to one another in the calculated way, and thus further enhancing the "on target" reliability.

In modifications of the invention, display means are provided with which the data supplied by the locating means are graphically displayed, preferably in the form of a perspective illustration that contains the motion path of the region to be charged with the focused acoustic waves and also contain the contours of the focus zone. The presentation, however, can also ensue in the form of a two-dimensional image wherein the third dimension is illustrated by different chromatic values, or gray-scale values. Regardless of how the graphic presentation ensues in detail, it is preferable to graphically emphasize the current position of the subject to be charged with the focused acoustic waves.

DESCRIPTION OF THE PREFERRED EMBODIMENTS

Figure 1:
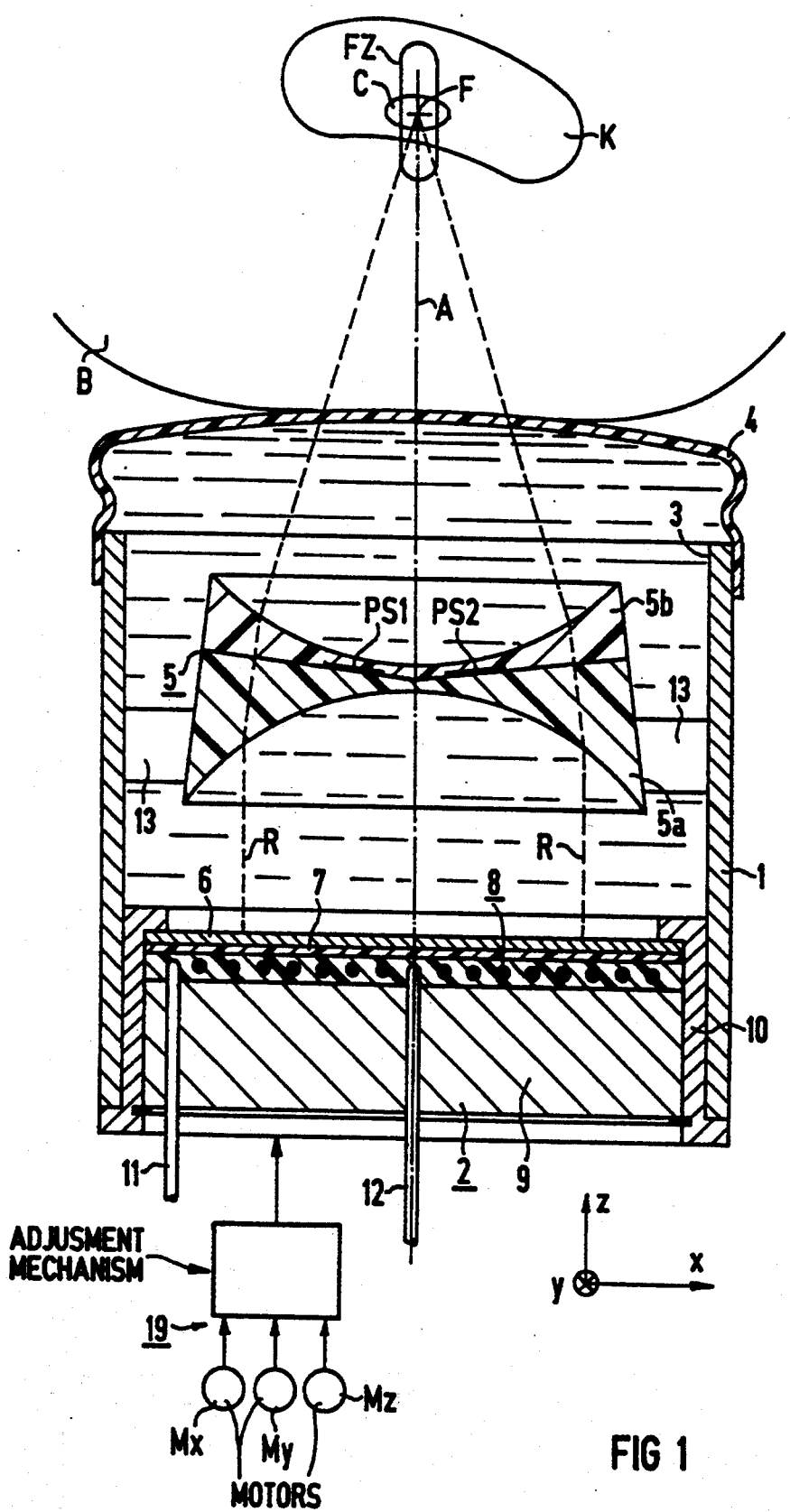
FIG. 1 is a schematic illustration of a longitudinal section through the shockwave source of a therapy system of the invention, the shockwave source containing an acoustic locating means.

The invention is illustrated in the drawings discussed below with reference to the example of therapy system for non-invasively disintegrating calculi, the sources of acoustic waves being acoustic pressure pulse sources fashioned as shockwave sources.

The shockwave source of the therapy system of the invention according to FIG. 1 has a tubular housing 1 with a shockwave generator generally referenced 2, arranged at one end. An exit opening 3 for acoustic pressure pulses emanating from the shockwave generator 2 is located at the other end of the housing 1, the exit opening 3 being closed with a flexible sack 4. The space surrounded by the shockwave generator 2, by the housing 1, and by the flexible sack 4 contains water, for example, as the liquid acoustic propagation medium for the pressure pulses emanating from the shockwave generator 2. These pressure pulses gradually intensify to form shockwaves along their propagation path as a consequence of the non-linear compression properties of the propagation medium. Regardless of whether a pressure pulse has in fact already intensified to form a shockwave, the term shockwave shall always be employed below for the sake of simplicity.

A positive acoustic lens 5, arranged in the propagation medium, is provided for focusing the shockwaves emanating from the shockwave generator 2. The positive acoustic lens 5 focuses the shockwaves onto a focus zone FZ lying on the acoustic axis A of the shockwave source which is identical to the center axis of the shockwave source, the center of this focus zone FZ being referenced F. The contour of the focus zone FZ shown in FIG. 1 surrounds that region within which the pressure of the shockwaves is at least equal to half the maximum (peak) pressure arising in the focus zone FZ (i.e., indicates an isobar for a −6 dB zone).

The shockwave source can be pressed with the flexible sack 4 against the (schematically indicated) body B of a patient for acoustic coupling. The shockwave source is thereby aligned such that the calculus C to be disintegrated which is located in the body B of the patient, for example the stone of a kidney K, is located in the focus zone FZ. As described in greater detail below, this occurs by receiving and evaluating parts of shockwaves generated with the shockwave generator 2 that are reflected at the calculus C to be disintegrated. The reflected parts are spherical diffraction waves. In addition, an x-ray means (not shown), or an ultrasound locating means (not shown) that preferably contains an ultrasound sector applicator, can additionally be provided in a known way.

An electromagnetic shockwave generator is provided as shockwave generator 2, this type of shockwave generator being set forth in greater detail, for example, in U.S. Pat. No. 4,674,505. The shockwave generator 2 has a circular disc-shaped, planar membrane 6 composed of an electrically conductive material that has one side directly adjoining the water enclosed in the shockwave source. A planar spiral coil 8 is applied on a coil carrier 9 composed of an electrically insulating material, arranged lying opposite the other side of the membrane 6, with an insulating foil 7 disposed between the coil 8 and the membrane 6. An electrically insulating casting compound is located between the spirally proceeding turns of the coil 8. These components of the shockwave generator 2 are accepted in the bore of a mounting ring 10 in axially non-displaceable fashion. The mounting ring 10 is in turn held non-displaceably in the bore of the housing 1.

The coil 8 has two terminals 11 and 12 via which it is connected to a high voltage pulse generator (not shown in FIG. 1). The pulse generator charges the coil 8 with high-voltage pulses. When it is charged with a high-voltage pulse, the coil 8 builds up a magnetic field extremely quickly. As a result, a current flowing opposite the current in the coil 8 is induced in the membrane 6, and consequently an opposing magnetic field is generated, which causes the membrane 6 to be suddenly moved away from the pancake coil 8. As a result, a planar shockwave is introduced into the water situated in the shockwave source.

The positive lens 5 provided for the focusing of the planar shockwaves is a biconcave lens that is essentially rotationally-symmetrical relative to the acoustic axis A, and is formed of a material, for example polystyrol, wherein the speed of sound is higher than in the water provided as the acoustic propagation medium. The positive lens 5 is secured in the bore of the housing 1 with a plurality of brackets 13, two of which are visible in FIG. 1. The positive lens 5 is composed of two lens parts 5a and 5b as can be seen from FIG. 2. The seam between the two lens parts 5a and 5b is a surface that is rotationally symmetrical relative to the acoustic axis A, and which can be "opened" into a plane, namely a conical surface in the case of the exemplary embodiment, whose center axis corresponds to the acoustic axis A.

Three pressure sensors PS1, PS2 and PS3 are applied by gluing to the concave, conical interface of the lens part 5A. These three pressure sensors PS1, PS2 and PS3 serve the purpose of receiving the pans of the shockwaves generated by the shockwave generator 2 which are reflected at the calculus C to be disintegrated, and generating (emitting) corresponding electrical signals. The pressure sensors PS1, PS2 and PS3 are piezoelectrically activated polyvinylidene fluoride (PVDF) foils that are provided with electrodes and which, as viewed in the direction of the acoustic axis A, each have the shape of an annulus sector extending over barely 120°, whereby the annulus sectors are congruent. Via signal lines that are not shown in FIG. 1, the pressure sensors PS1 through PS3 are in communication with evaluation and drive electronics (not shown in FIG. 1). As a consequence of the fashioning of the interface (seam) between the lens parts 5a and 5b as a surface that can be opened into a plane, the pressure sensors PS1 through PS3 can be applied unproblematically, particularly without the risk of the formation of folds. The two lens parts 5a and 5b are glued to one another with a suitable adhesive. Since the thickness of the pressure sensors lies on the order of magnitude of 200 μm, the adhesive is capable without further difficulty of bridging the gap between the two lens parts 5a and 5b outside the pressure sensors PS1 through PS3. It is also possible, however, to apply the pressure sensors PS1 through PS3 on the convex, conical interface of the lens part 5b.

A schematically indicted adjustment mechanism 19, having electric motors Mx, My and Mz, is allocated in FIG. 1 to the shockwave source. The adjustment mechanism 19 contains, for example, gearings or the like in a known way and serves the purpose of adjusting the shockwave source in the direction of the axes of the rectangular, spatial coordinate system entered in FIGS. 1 and 2. The motor Mx is thereby responsible for the adjustment in the direction of the x-axis; the motor My is responsible for the adjustment in the direction of the y-axis and the motor Mz is responsible for the adjustment in the direction of the z-axis of the coordinate system. The z-axis, moreover, corresponds to the acoustic axis A that proceeds through the center F of the focus zone FZ. The y-axis proceeds parallel to the angle bisector of the pressure sensor PS3.

Figure 2:
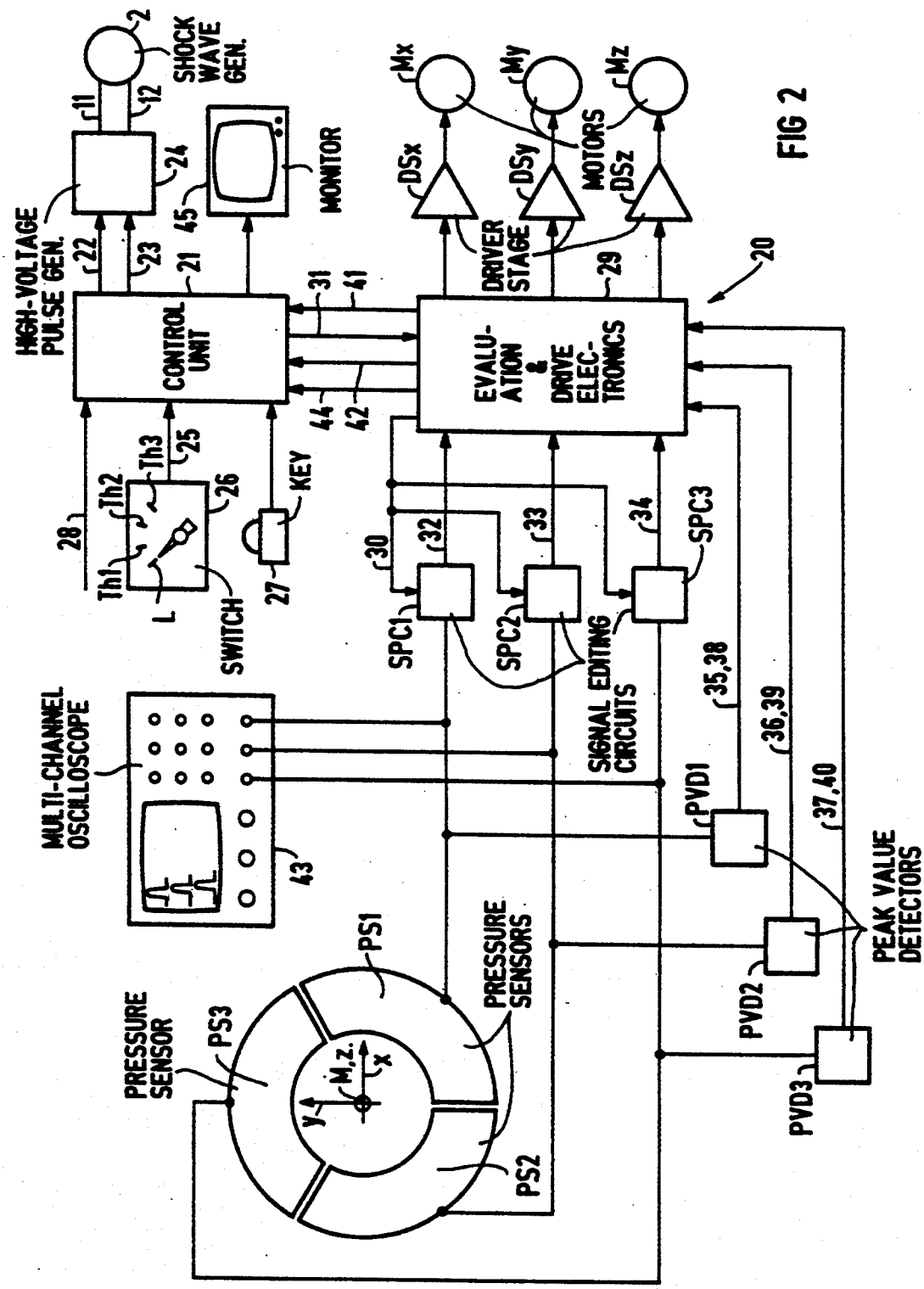
FIG. 2 is a front view of the pressure sensor arrangement of the acoustic locating means shown in FIG. 1 and a schematic block circuit diagram of the therapy system of the invention.

As shown in FIG. 2, the pressure sensors PS1 through PS3 are connected to the aforementioned evaluation and control electronics 20, which is in turn connected to a control unit 21. A high-voltage pulse generator 24 is in communication with the control unit 21 via two control lines 22 and 23, the schematically indicated shockwave generator 2 being connected to this high-voltage pulse generator 24 via the terminals 11 and 12. A switch 26 with which the therapy system can be optionally switched into the locating mode or into the therapy mode, is also connected to the control unit 21 via a line 25. In FIG. 2, the switch 26 is shown in its position referenced L for the locating mode. Its other positions, which correspond to three types of therapy mode, are referenced Th1 through Th3. When the switch 26 assumes its position L for the locating mode, it initiates the control unit 21 via the control line 22 to drive the high-voltage pulse generator 24 to generate shockwaves, the fundamental wave thereof having a frequency that is greater by a factor of 2 through 10 than the frequency of the fundamental wave of the shockwaves generated for therapy. The amplitude of the shockwaves generated in the locating mode is also greatly reduced in comparison to the amplitude of the shockwaves serving the purpose of therapy, namely to such an extent that the shockwaves still have a peak pressure on the order of magnitude of a few bar in the region of the calculus. The peak pressures of the shockwaves for the therapy lie on the order of magnitude of few 100 bar. The frequency of the fundamental wave of the shockwaves generated for therapy lies on the order of magnitude of 100 kHz through 1 MHz. Of course, the shockwaves serving for therapy as well as the shockwaves serving for locating also have higher-frequency components since the shockwaves are extremely broadband signals. The low-intensity shockwaves generated for locating, having a higher frequency fundamental wave, are referred to below as locating shockwaves, and the higher-intensity shockwaves generated for therapy having a lower frequency fundamental wave, are referred to as therapy shockwaves. If the high-voltage pulses required for generating the shockwaves are produced by capacitor discharges, the locating shockwaves can be realized by using, for example, a lower capacitance, that may possibly be charged to a lower voltage, than is the case when generating the therapy shockwaves. The employment of locating shockwaves having an increased frequency of the fundamental wave compared to the therapy shockwaves offers the advantage, among other things, of a better topical resolution, since the size of the focus zone is inversely proportional to the frequency of the fundamental wave.

In the locating mode, the control unit 21 activates the high-voltage pulse generator 24 to drive the shockwave generator 2 for emitting locating shockwaves having a repetition rate on the order of magnitude of a few 10 through a few 100 Hz. The control unit 21 supplies the corresponding trigger pulses to the high-voltage pulse generator 24 via the control line 23. During the therapy mode, there is the optional possibility, by actuating a key 27, to trigger individual therapy shockwaves, or to supply trigger pulses to the control unit 21 via a trigger line 28 in a known way which are derived from a periodic body function of the patient, for example from the respiratory and/or cardiac activity thereof. In the therapy mode (the differences between the individual types of therapy mode shall be set forth later), the emission of the therapy shockwaves thus ensues with a substantially lower repetition rate than does the emission of the locating shockwaves during the locating mode.

The evaluation and control circuit 20 includes peak value detectors PVD1 through PVD3 and signal editing circuits SPC1 through SPC3, to which the output signals of the pressure sensors PS1 through PS3 are respectively supplied. The peak value detectors PVD1 through PVD3 and the signal editing circuits SPC1 through SPC3 are driven by a control and time-measuring unit 29, belonging to the evaluation and drive circuit 20, via a control line 30 such that their inputs are inhibited after a shockwave has been produced for a time that is at least equal to the propagation time of the shockwave from the shockwave generator 2 through the positive lens 5 and which is not substantially longer than the propagation time of the shockwave from the shockwave generator 2 to the calculus C to be disintegrated. The control and time-measuring unit 29 receives the clock signals required for this purpose from the control unit 21 via a line 31. Only those parts of the output signals of the pressure sensors PS1 through PS3 are thus taken into consideration that represent the spherical diffraction wave emanating from the calculus C to be disintegrated after being charged with a shockwave. These signal parts are converted into square-wave pulses in the identical signalling editing circuits SPC1 through SPC3, for example with a Schmitt trigger having a variable trigger threshold. These square-wave pulses are supplied via lines 32 through 34 to the control and time-measuring unit 29. The unit 29 measures the pulse width of the square-wave pulses, which represent the pulse width of the acoustic signals received by the pressure sensors PS1 through PS3. The trigger threshold of the Schmitt triggers contained in the signal editing circuits SPC1 through SPC3, for example, is selected such that it roughly corresponds to one-tenth of the minimally anticipated peak amplitude of the electrical signals supplied by the pressure sensors PS1 through PS3.

Following the generation of a locating shockwave, the respective peak value detectors PVD1 through PVD3 calculate the peak value of the resulting output signals of the pressure sensors PS1 through PS3, and emit a corresponding signal to the control and time-measuring unit 29 via lines 35 through 37. Via lines 38 through 40, they each also forward a pulse identifying the point in time of the occurrence of the respective peak value to the control and time-measuring unit 29. For clarity, all lines 35 through 40 are not shown in FIG. 2; each line bears two reference numerals, for example 35, 38.

On the basis of the output signals of the signal editing circuits SPC1 through SPC3 and of the peak value detectors PVD1 through PVD3, the control and time-measuring unit 29 calculates with reference to the coordinate system entered in FIGS. 1 and 2, the spatial position that the calculus C to be disintegrated assumed for every locating shockwave emitted in the locating and therapy mode upon incidence of the locating shockwave. The corresponding data are supplied to the control unit 21 via a line 41.

The control and time-measuring unit 29 makes use of the fact that the signal shape (i.e. peak amplitude and pulse width of the output signals of the pressure sensors PS1 through PS3) and the chronological delay with which the output signals of the pressure sensors PS1 through PS3 appear after the triggering of a shockwave, allow an identification of the spatial position of the calculus C to be disintegrated.

Figure 3:
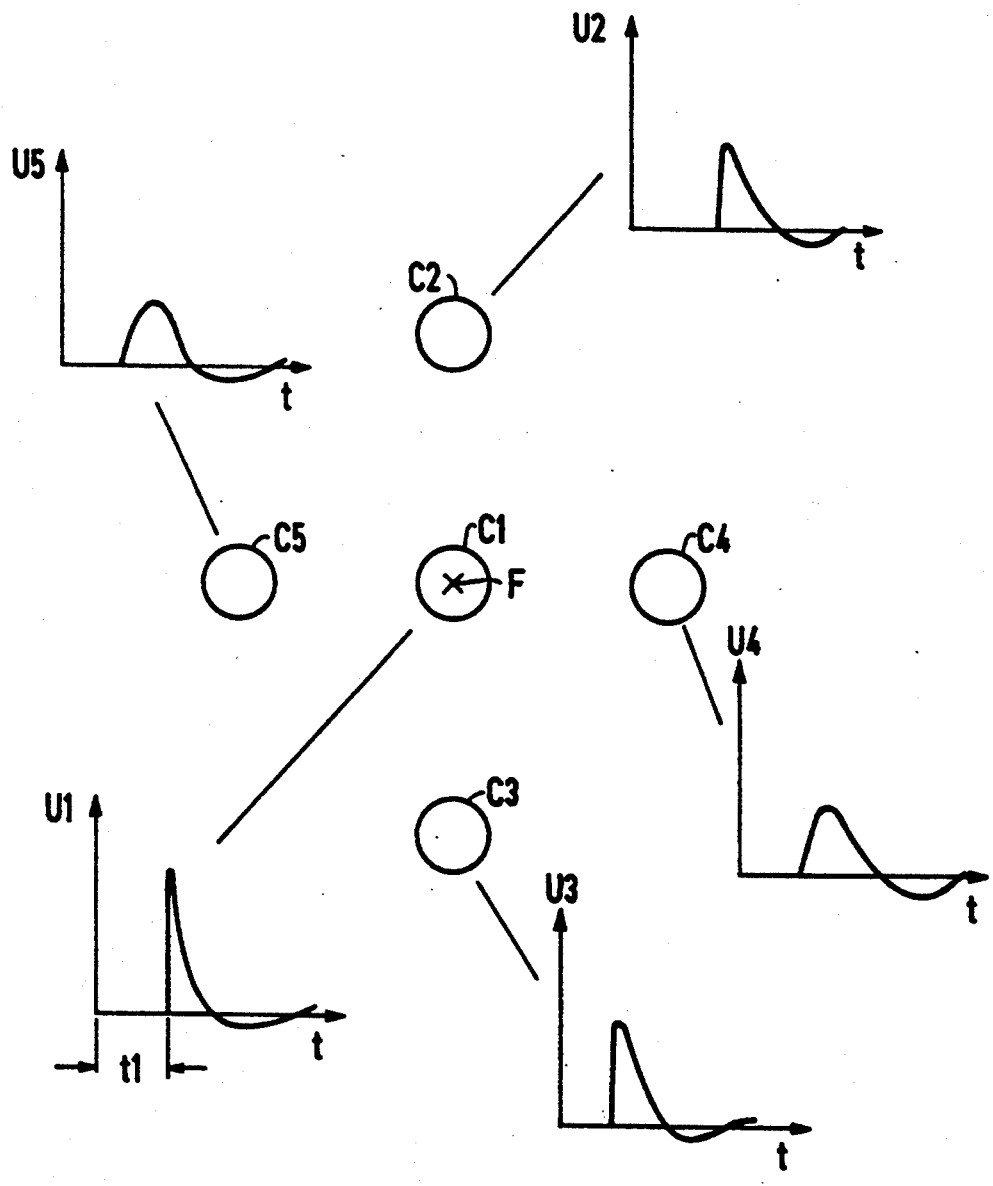
FIG. 3 is a schematic illustration of the respective output signals of one of the pressure sensors arising for different positions of the focus of the shockwaves relative to a calculus to be disintegrated.

This is schematically illustrated in FIG. 3 which shows the output signals U1 through U5 of the pressure sensor PS3 over time c for different positions C1 through C5 of the calculus C to be disintegrated with reference to the center F of the focus zone. It is clear that the output signal of the pressure sensor PS3 has a lower peak amplitude and a greater a pulse width as the calculus C to be disintegrated lies farther from the center F of the focus zone. It is also clear that the time span which elapses between the generation of a locating shockwave and the appearance of the output signal of the pressure sensor PS3 generated by the corresponding diffraction wave deviates from the time span t1 that arises when the calculus to be disintegrated is located in the center F of the focus zone (see position C1 in FIG. 2) to an extent correlated with the distance from the center F along the z-axis. A decrease of the time span t1 corresponds to a position of the calculus C to be disintegrated that is too close to the shockwave generator 2, whereas an increase of the time span t1 corresponds to a position of the calculus C to be disintegrated that is too far from the shockwave generator 2.

The above comments correspondingly apply to the pressure sensors PS1 and PS2. It is thus clear that the control and time-measuring unit 29—given an appropriate structure—is capable of identifying the spatial position of the calculus C to be respectively disintegrated. The structure of the evaluation and drive electronics 20 is not described in detail since a person skilled in the art can without further difficulty design and construct such circuitry on the basis of his other technical expertise and with reference to the functioning thereof disclosed herein.

As a consequence of the fact that the repetition rate of the locating shockwaves is high in comparison to the frequency with which the calculus C to be disintegrated moves, and is also so high that the distances the calculus to be disintegrated traverses between two successive locating shockwaves lie at most on the order of magnitude of the dimensions of the calculus C, the spatial position of the calculus C to be disintegrated is known at quasi-arbitrary points in time, namely with a precision that lies on the order of magnitude of the dimensions of the calculus C to be disintegrated. This is also valid when the position of the calculus C lies outside the focus zone FZ. It is thus possible to achieve an "on target" reliability that is substantially enhanced compared to the prior art during the therapy mode of the therapy system of the invention.

In addition to the generation of locating shockwaves during the therapy mode, which is continued in the way set forth in conjunction with the locating mode, the high-voltage pulse generator 24 is driven by the control unit 21 when the key 27 is actuated or when a trigger pulse arrives via the trigger line 28, so that it charges the shockwave generator 2 with a corresponding high-voltage pulse to generate a therapy shockwave. The types of therapy mode allocated to the positions of the switch 26 referenced Th1 through Th3 differ but still assure that the calculus C to be disintegrated is located in the focus zone of the therapy shockwaves.

When the switch 26 is in its position referenced Th1, the control and measurement unit 29 drives the electric motors Mx through Mz of the adjustment mechanism 19 via the driver stages DSx through DSz belonging to the evaluation and drive electronics 20 such that the center F of the focus zone FZ of the therapy shockwaves coincides with those coordinates that the control and time-measuring unit 29 had calculated on the basis of the output signals of the pressure sensors PS1 through PS3 belonging to the most recent locating shockwave. This mode is particularly suited for treatments wherein the calculus C to be disintegrated moves only slightly and/or is large in comparison to the dimensions of the focus zone FZ. In such treatments, the motion of the calculus C to be disintegrated, which occurred between the last locating shockwave emitted before therapy shockwave and the incidence of the therapy shockwave on the calculus C, is so slight that no noteworthy degradation of the "on target" reliability occurs.

In treatments wherein one must expect considerable movements of the calculus C in the time span elapsing between the incidence of the last locating shockwave emitted before a therapy shockwave and the incidence of the therapy shockwave on the calculus C to be disintegrated, and/or wherein the dimensions of the calculus C to be disintegrated lie on the order of magnitude of the dimensions of the focus zone of the therapy shockwaves, it is recommended to select that operation of the therapy mode that corresponds to that position of the switch 26 referenced Th2. In this mode, the control and time-measuring unit 29 calculates the spatial position of the calculus C to be disintegrated on the basis of the output signals of the pressure sensors PS1 through PS3 in advance as a function of the time and drives the electric motors Mx through Mz of the adjustment mechanism 19 such that the spatial position of the center F of the focus zone FZ of the therapy shockwaves coincides at all times with the position of the calculus C to be disintegrated that has been calculated in advance for this point in time. There is then an extremely high probability that the calculus Z to be disintegrated will also be located in the focus zone FZ when the therapy shockwaves arrive in their focus zone FZ, so that an extremely high "on target" reliability is assured. It is clear that this mode is only suitable for those treatments wherein the calculus C to be disintegrated executes an essentially periodic motion, since a pre-calculation of the spatial position of the calculus C to be disintegrated would otherwise not be possible with adequate precision. It is also clear that the pre-determination of the spatial position of the calculus C to be disintegrated can only ensue with adequate precision when the motion of the calculus C to be disintegrated was "observed" over a few periods during locating mode. The circuit part of the control and time-measuring unit 29 responsible for the pre-calculation of the spatial position of the calculus C to be disintegrated can, moreover, be constructed using fuzzy logic.

The spatial position of the calculus C to be disintegrated is also pre-calculated with the control and measurement unit 29 in the type of therapy mode described with the position of the switch 26 referenced Th3. In this mode, the control and time-measuring unit 29 evaluates the signals supplied to it in order to calculate a position for which there is a maximum dwell probability of the calculus C to be disintegrated. The control and time-measuring unit 29 then drives the electric motors Mx through Mz of the adjustment mechanism 19 such that the center F of the focus zone FZ of the therapy shockwaves coincides with the position of maximum dwell probability. When the pre-calculated position of the calculus C to be disintegrated coincides with the position of maximum dwell probability, the control and time-measuring unit 29 forwards a corresponding signal to the control unit 21 via a line 42. Upon actuation of the key 27 or the arrival of a trigger pulse via the trigger line 28, this effects the emission of a therapy shockwave only when the signal simultaneously supplied to it via the line 42 indicates that the calculus C to be disintegrated is located in its position of maximum dwell probability, and thus in the focus zone of the therapy shockwaves. This last-described operation of the therapy mode is particularly suitable for those treatments wherein the amplitude of the motion and/or the dimensions of the calculus C to be disintegrated lie at most on the order of magnitude of the dimensions of the focus zone of the therapy shockwaves.

For implementing a treatment, one proceeds such that the shockwave source of the therapy system is first aligned relative to the body B of the patient such that the calculus C to be disintegrated is located in the proximity of the focus zone of the therapy shockwaves. This can ensue either with the assistance of an additionally, known locating means operating on an x-ray and/or ultrasound basis or can ensue exclusively on the basis of the output signals of the pressure sensors PS1 through PS3. If these output signals are used, the shockwave source is adjusted relative to the body B of the patient in the nature of a scan motion until the output signals of the pressure sensors PS1 through PS3 that are presented in-phase above one another on a multi-channel oscilloscope 43, indicate the presence of the calculus C to be disintegrated in the region of the focus zone FZ. When the described, rough alignment of the shockwave source relative to the body B of the patient has ensued, the control and time-measuring unit 29 is activated, which identifies and pre-calculates the position of the calculus C to be disintegrated on the basis of the signals supplied to it. After a certain "response time", the therapy means can be switched with the switch 26 to the operation of the therapy mode that corresponds to the selected treatment. The control and time-measuring unit 29 then drives the electric motors Mx through Mz in a manner corresponding to the operation of the selected therapy mode. When this has been completed, the control and time-measuring unit 29 forwards a corresponding signal via a line 44 to the control unit 21, which only then permits the emission of therapy shockwaves.

Figure 4:
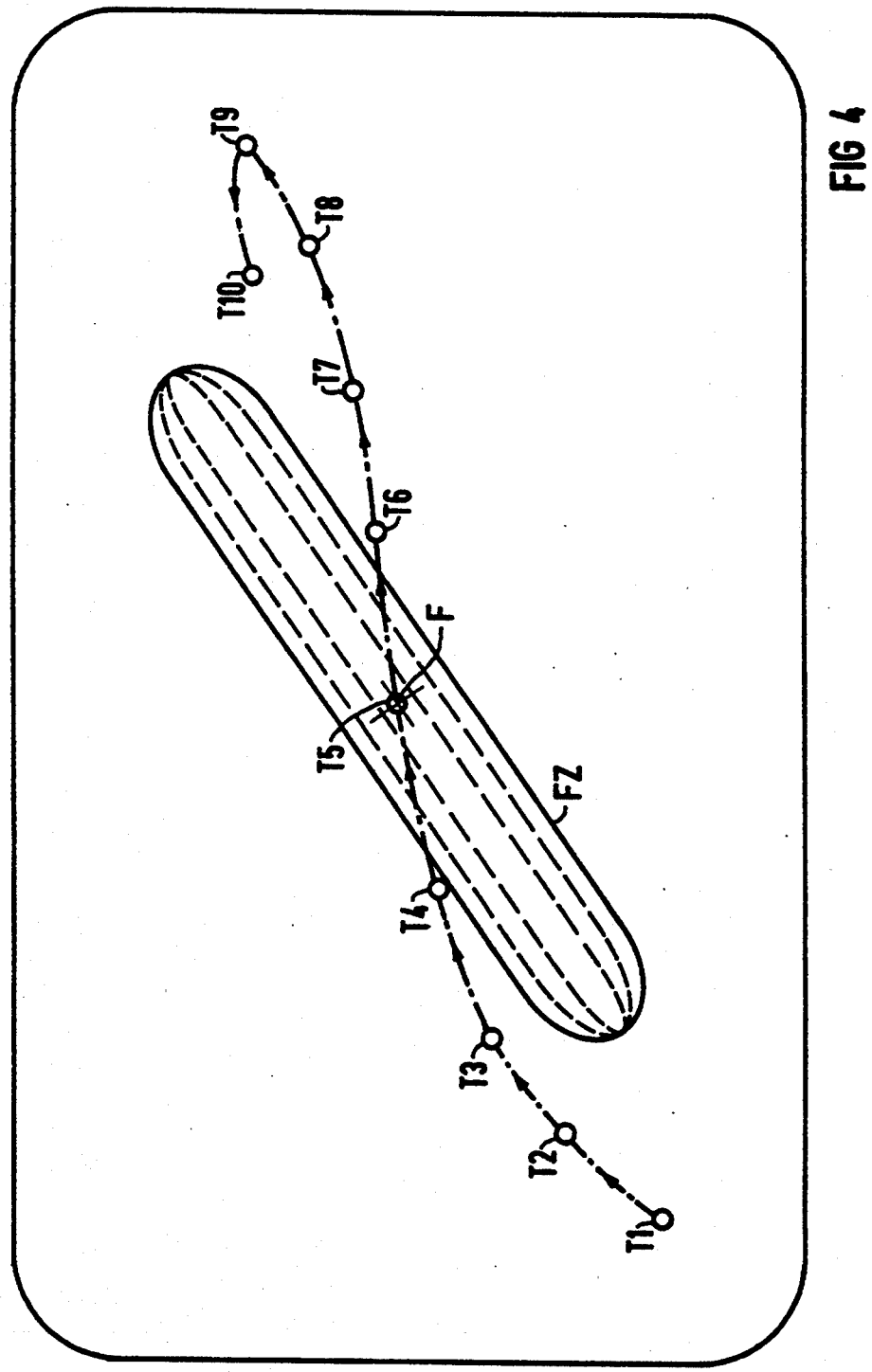
FIG. 4 shows a picture screen image of the display means of the therapy system of the invention arising during operation of said therapy apparatus.

In order to be able to monitor the locating or the therapy procedure, a monitor 45 is connected to the control unit 21, the focus zone FZ being imaged in a perspective illustration on the picture screen thereof, as shown in FIG. 4. The movement of the calculus C to be disintegrated, over a defined time span of, for example, one-half second, is also shown on the monitor 45 using the data supplied to the control unit 21 via the line 41. When the therapy system is in locating mode or in that type of therapy mode corresponding to the switch position Th1, then the motion of the calculus C to be disintegrated is shown on the monitor for, for example, the past half second. In those types of the therapy mode corresponding to the switch positions Th2 and Th3, the monitor picture respectively shows the motion of the calculus to be disintegrated for, for example, the past quarter second and shows the pre-calculated movement of the calculus to be disintegrated for, for example, the following quarter second. The cigar-shaped focus zone FZ is shown in the monitor picture. The center of the focus zone F is also marked by a cross. The movement of the calculus to be disintegrated is indicated by a dot-dash line, and the direction of the movement of the calculus is illustrated by arrow symbols. The positions of the calculus to be disintegrated that correspond to the points in time at which locating shockwaves are generated are illustrated by circular symbols and are referenced T1 through T10. In the locating mode and in the type of therapy mode described first, the positions T1 through T10 are the positions that respectively correspond to the ten most recent locating shockwaves. In the types of the therapy mode described last, the positions T1 through T5 are the positions respectively corresponding to the five most recent locating shockwaves. The positions T6 through T10 are those positions that were pre-calculated for the points in time of the next five locating shockwaves (yet to be generated).

The motion path connecting the positions T1 through T10 is calculated by the control and time-measuring unit 29 according to known approximation (curve-fitting and interpolation) methods.

Figure 5:
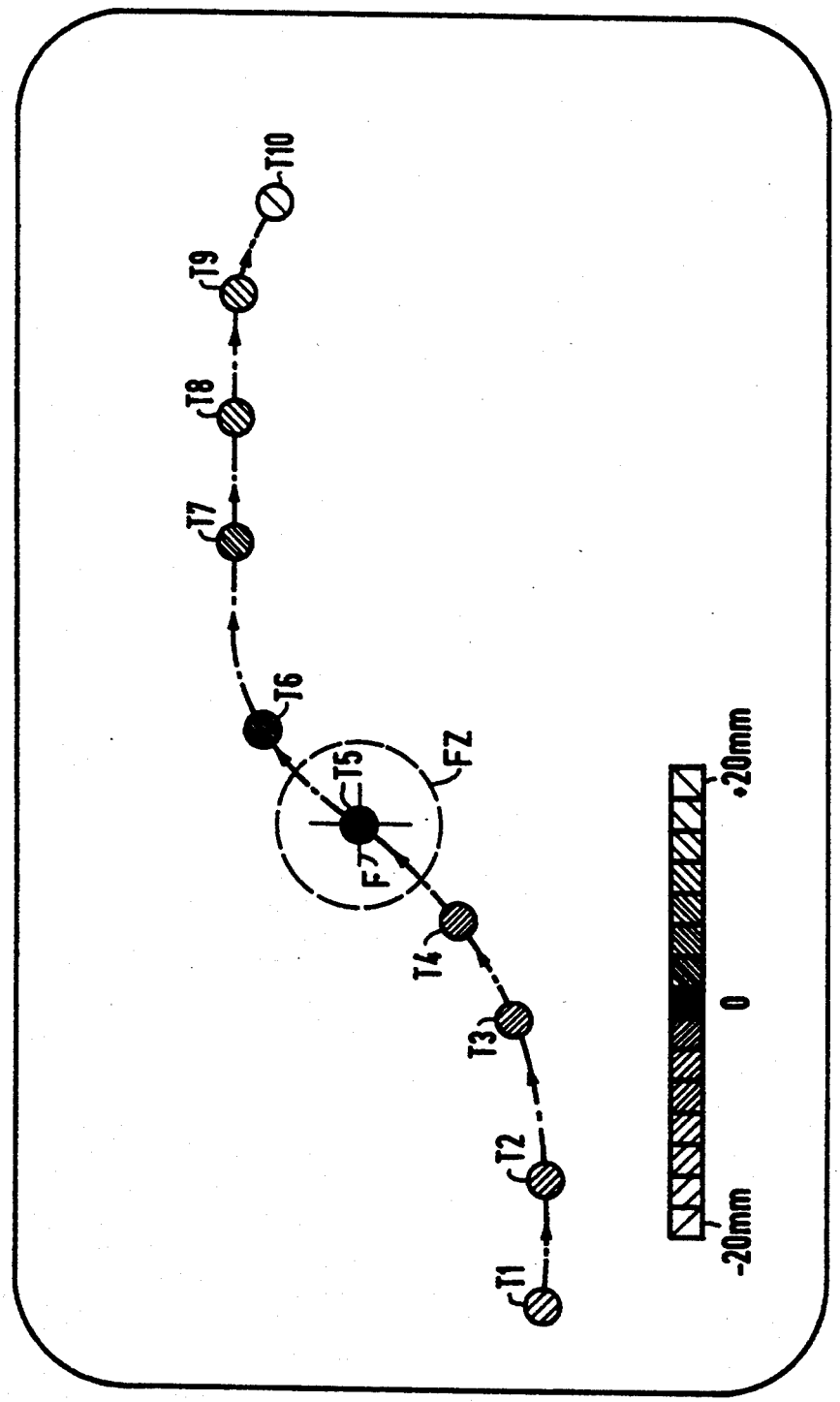
FIGS. 5 and 6 respectively show modifications of the therapy system of the invention in an illustration analogous to that of FIG. 4.

FIG. 5 shows a further embodiment of a therapy system of the invention that differs from that set forth above only in the presentation on the monitor. By contrast to the above-described exemplary embodiment, the focus zone FZ is not shown in perspective. On the contrary, only the projection of the focus zone FZ in the direction of the acoustic axis A is shown with broken lines and the center F of the focus zone FZ is shown as a cross. As in the case of the above-described exemplary embodiment, ten positions of the calculus to be disintegrated are shown, again being referenced T1 through T10 and corresponding to the points in time at which locating shockwaves are emitted. Those positions are derived by parallel projection parallel to the acoustic axis A. The positions, or the movement of the calculus to be disintegrated with respect to the focus zone FZ, or the center F thereof, are then reproduced in the projection plane that proceeds parallel to the plane containing the x-axis and the y-axis. In order to be able also to illustrate the position of the individual positions T1 through T10 of the calculus to be disintegrated with reference to the focus zone FZ (or the center F thereof in the direction of the z-axis coinciding with the acoustic axis), the positions T1 through T10 are shown in gray-scale values or chromatic values that illustrate their distance from the center F of the focus zone FZ in the direction of the z-axis. In the case of FIG. 4, this is illustrated by different densities of cross-hatching, whereby the cross-hatching is the denser the shorter the distance of the calculus to be disintegrated from the center F of the focus zone FZ, measured in the direction of the z-axis. The cross-hatching runs from upper left to bottom right for positions of the calculus to be disintegrated that lie between the shockwave source and the center F of the focus zone FZ. The cross-hatching proceeds from upper right to bottom left for positions of the calculus to be disintegrated that lie beyond the center F of the focus zone FZ. When the calculus to be disintegrated has the distance zero from the center F of the focus zone FZ as viewed in the direction of the z-axis, the corresponding position is shown black (the position T5 in FIG. 5). A bar is mixed in at the lower edge of the image of the monitor 45, from which bar the allocation between the various grayscale values or chromatic values and the distance from the center F of the focus zone FZ measured in the direction of the z-axis can be read, this being illustrated in the case of FIG. 5 by different cross-hatching densities and directions, as in the case of the positions T1 through T10.

Figure 6:
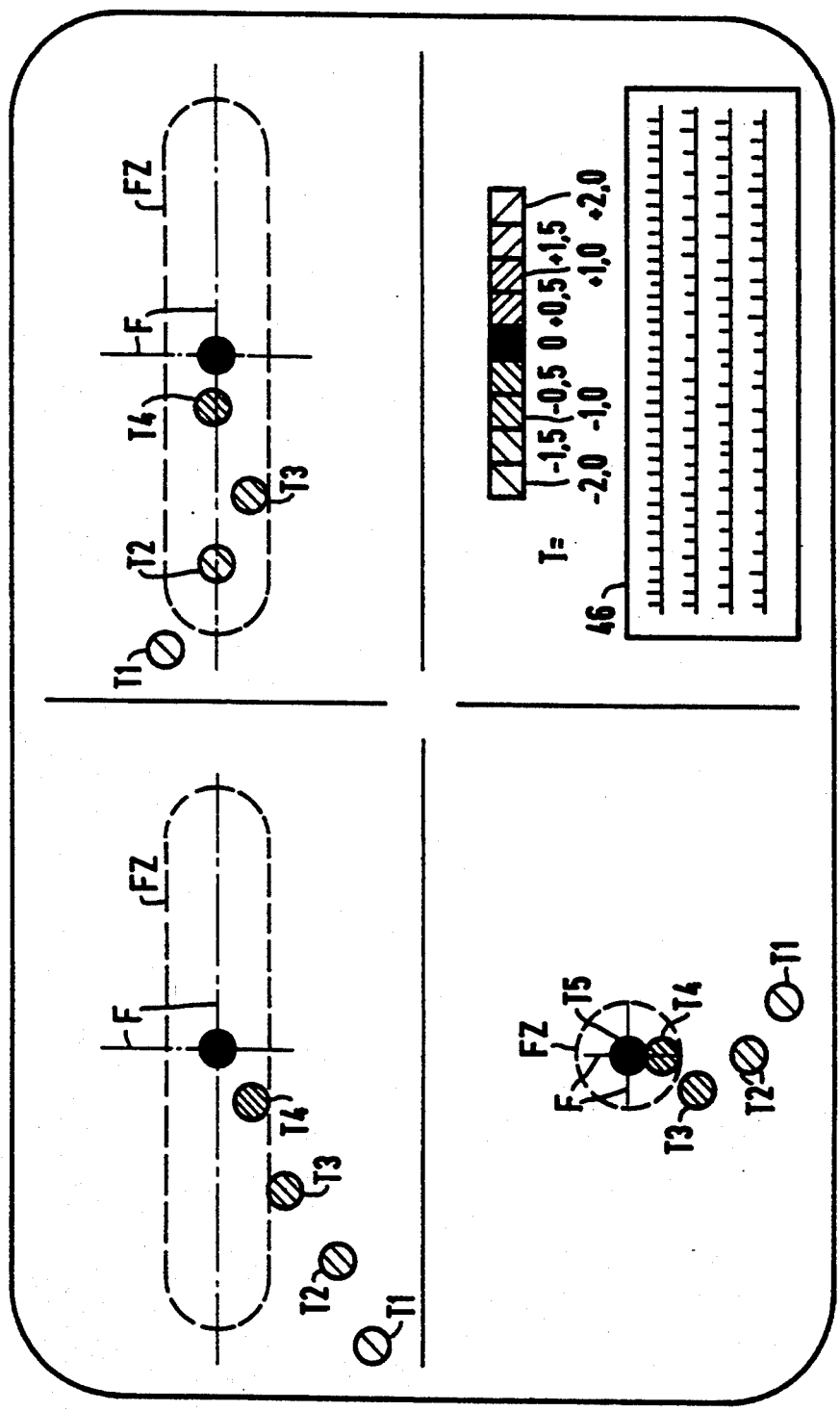

FIG. 6 illustrates another exemplary embodiment, this likewise differing from the therapy means set forth first only on the basis of the nature of the picture screen picture of the monitor 45. In the exemplary embodiment of FIG. 6, the picture screen is divided into quadrants. The upper left quadrant shows the focus zone FZ and the positions T1 through T5 of the calculus to be disintegrated in parallel projection relative to the x-axis for the points in time of generating five locating shockwaves. The upper right quadrant shows this information in parallel projection relative to the y-axis and the bottom left quadrant shows this information in parallel projection relative to the z-axis. The spatial position of the individual positions T1 through T5 relative to the focus zone FZ (or the center F thereof) thus arises from the three projections. In order to facilitate the allocation of the individual positions T2 through T9 to one another in the three projections, different grayscale values or chromatic values are allocated to specific points in time, so that any one position has the respectively same grayscale value or chromatic value in the three projections. This is illustrated in FIG. 6 by different cross-hatching densities and directions.

An appropriate scale is mixed into the monitor picture at the bottom right quadrant, showing the allocation between grayscale value or chromatic value and time, whereby the point in time "zero" respectively corresponds to the momentary (current) point in time. As may be derived from the scale, the therapy means for the monitor picture shown in FIG. 6 is either in the locating mode or in the first type of therapy mode, since no precalculated positions for the calculus to be disintegrated are shown; these would be recognizable on the basis of a cross-hatching direction proceeding from upper left to bottom right.

There is also the possibility at the bottom right quadrant in the screen picture of mixing alpha numerical particulars, for example with respect to the dimensions of the focus zone, in a field referenced 46. Information can also be mixed-in indicating an alignment of the shockwave source relative to the body B of the patient for which an enhanced dwell probability of the calculus to be disintegrated in the focus zone FZ occurs.

Such an alignment is calculated by the control and time-measuring unit 29.

In the exemplary embodiment of FIGS. I through 3, the aperture angle of the scan between the two lens parts 5a and 5b is selected such that the scan represents a good approximation in that region in which the pressure sensors PS1 through PS3 are arranged to the shape of the wave front in the lens 5 exhibited by a spherical diffraction wave emanating from the calculus C. In this case, the maximum differences in transit time that can occur between the different locations of the pressure sensors PS1 through PS3 and the center F of the focus zone FZ are only slight, so that only an insignificant spread of the output signals of the pressure sensors PS1 through PS3 occurs in comparison to an ideally-shaped seam (which can only be realized with high outlay); this spread does not have any noteworthy influence on the obtainable topical resolution.

Moreover, the topical resolution that can be obtained becomes better as the area of the pressure sensors becomes smaller; here, however, a compromise must be made between the obtainable topical resolution and the sensitivity of the pressure sensors, which increases with increasing area. If punctiform pressure sensors were employed, moreover, an exact locating would be possible only by measuring transit time, i.e., without evaluating the pulse width and the peak amplitudes. Since, however, the pressure sensors must necessarily have a finite expanse, the additional evaluation of the aforementioned quantities is required in the way set forth.

The calibration of the locating means of the therapy system, moreover, preferably ensues with a phantom that contains a target member, for example a steel ball, arranged at an exactly known position in a suitable acoustic propagation medium, for example water.

Arrangements of the pressure sensors that deviate from the arrangement set forth are also possible. Thus, for example, the pressure sensors (in a way not shown) can be arranged between the positive lens 5 and the shockwave generator 2, preferably in a plane that intersects the acoustic axis A at a right angle. There is also the possibility of placing the pressure sensors on that end face of the positive lens 5 that faces toward the focus zone FZ or toward the shockwave generator 2. There is also basically the possibility of arranging pressure sensors within the shockwave source in a suitable surface between the focus zone FZ and the acoustic positive lens 5.

Three pressure sensors PS1 through PS3 are present in the exemplary embodiments that have been set forth,, however, more than three pressure sensors can be provided. In particular, it can be advantageous to provide a plurality of ring arrangements of each having three annulus sector-shaped pressure sensors concentric relative to the acoustic axis A, preferably arranged in a common plane or surface.

The described exemplary embodiments are directed exclusively to a therapy system having a shockwave source as the source of focused acoustic waves. Other acoustic pressure pulse generators, however, can be provided instead. There is also the possibility of providing a therapeutic ultrasound source as the source of acoustic waves, for instance as is used in hyperthermia. Such an ultrasound source does not emit the ultrasound waves as pressure pulses but as continuous sound.

The exemplary embodiments that have been set forth are directed to the employment of a therapy system of the invention in conjunction with the disintegration of calculi. Other applications, of course, are possible, such as, for example, the aforementioned hyperthermia, the treatment of bone conditions and the treatment of tumors, particularly with negative pressure pulses.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy system for administering acoustic energy to a subject comprising:
    means for generating acoustic waves focused at a focus zone;
    means for effecting relative three-dimensional displacement between said focus zone and a subject to be treated with said focused acoustic waves; and
    locating means for non-invasively acquiring a three-dimensional spatial position of a region to be charged with said focused acoustic waves within said subject continuously as a function of time for controlling said means for effecting relative displacement such that said focus zone and said region are in substantial coincidence, at least when charging said region with said focused acoustic waves.

2. A therapy system as claimed in claim 1 wherein said means for effecting relative three-dimensional displacement comprises means for causing said focus zone to continuously follow movement of said region based on signals from said locating means.

3. A therapy system as claimed in claim 1 further comprising control and measurement means for predetermining said three-dimensional spatial position of said region based on signals from said locating means.

4. A therapy system as claimed in claim 3 wherein said control and measurement means comprises means operating based on fuzzy logic.

5. A therapy system as claimed in claim 3 further comprising means for triggering charging of said region with said focused acoustic waves when said predetermined position of said region coincides with said focus zone.

6. A therapy system as claimed in claim 1 further comprising control and measurement means for determining alignment of said means for generating acoustic waves and said subject based on signals from said locating means and on the geometry of said focus zone for enhancing the dwell probability of said focused acoustic waves in said region.

7. A therapy system as claimed in claim 1 further comprising display means for graphically displaying data generated by said locating means relating to said three-dimensional spatial position of said region and said focus zone.

8. A therapy system as claimed in claim 7 wherein said display means comprises means for displaying a perspective representation identifying a motion path of said region and containing the outline of said focus zone.

9. A therapy system as claimed in claim 7 wherein said display means comprises means for generating a two-dimensional image with a third dimension represented by different chromatic values.

10. A therapy system as claimed in claim 7 wherein said display means comprises means for generating a two-dimensional image with a third dimension illustrated by different grayscale values.

11. A therapy system as claimed in claim 7 wherein said display means includes means for graphically emphasizing a current position of said region.

12. A therapy system for administering acoustic energy to a subject comprising:
means for generating acoustic waves focused at a focus zone;
means for effecting relative three-dimensional displacement between said focus zone and a subject to be treated with said focused acoustic waves, said subject containing a region to be charged with said focused acoustic waves, said region moving at a frequency; and
locating means for non-invasively acquiring a three-dimensional spatial position of said region within said subject at a repetition rate which is at least twenty times higher than said frequency for controlling said means for effecting relative displacement such that said focus zone and said region are in substantial coincidence, at least when charging said region with said focused acoustic waves.

13. A therapy system as claimed in claim 12 wherein said means for effecting relative three-dimensional displacement comprises means for causing said focus zone to continuously follow movement of said region based on signals from said locating means.

14. A therapy system as claimed in claim 12 further comprising control and measurement means for predetermining said three-dimensional spatial position of said region based on signals from said locating means.

15. A therapy system as claimed in claim 14 wherein said control and measurement means comprises means operating based on fuzzy logic.

16. A therapy system as claimed in claim 14 further comprising means for triggering charging of said region with said focused acoustic waves when said predetermined position of said region coincides with said focus zone.

17. A therapy system as claimed in claim 12 further comprising control and measurement means for determining alignment of said means for generating acoustic waves and said subject based on signals from said locating means and on the geometry of said focus zone for enhancing the dwell probability of said focused acoustic waves in said region.

18. A therapy system as claimed in claim 12 further comprising display means for graphically displaying data generated by said locating means relating to said three-dimensional spatial position of said region and said focus zone.

19. A therapy system as claimed in claim 18 wherein said display means comprises means for displaying a perspective representation identifying a motion path of said region and containing the outline of said focus zone.

20. A therapy system as claimed in claim 18 wherein said display means comprises means for generating a two-dimensional image with a third dimension represented by different chromatic values.

21. A therapy system as claimed in claim 18 wherein said display means comprises means for generating a two-dimensional image with a third dimension illustrated by different grayscale values.

22. A therapy system as claimed in claim 18 wherein said display means includes means for graphically emphasizing a current position of said region.

23. A therapy system for administering acoustic energy to a subject comprising:
means for generating acoustic waves focused at a focus zone;
means for effecting relative three-dimensional displacement between said focus zone and a subject to be treated with said focused acoustic waves; and
locating means for non-invasively, repeatedly acquiring a three-dimensional spatial position of a region to be charged with said focused acoustic waves within said subject at time intervals of less than 0.25 seconds for controlling said means for effecting relative displacement such that said focus zone and said region are in substantial coincidence, at least when charging said region with said focused acoustic waves.

24. A therapy system as claimed in claim 23 wherein said means for effecting relative three-dimensional displacement comprises means for causing said focus zone to continuously follow movement of said region based on signals from said locating means.

25. A therapy system as claimed in claim 23 further comprising control and measurement means for predetermining said three-dimensional spatial position of said region based on signals from said locating means.

26. A therapy system as claimed in claim 25 wherein said control and measurement means comprises means operating based on fuzzy logic.

27. A therapy system as claimed in claim 25 further comprising means for triggering charging of said region with said focused acoustic waves when said predetermined position of said region coincides with said focus zone.

28. A therapy system as claimed in claim 23 further comprising control and measurement means for determining alignment of said means for generating acoustic waves and said subject based on signals from said locating means and on the geometry of said focus zone for enhancing the dwell probability of said focused acoustic waves in said region.

29. A therapy system as claimed in claim 23 further comprising display means for graphically displaying data generated by said locating means relating to said spatial position of said region and said focus zone.

30. A therapy system as claimed in claim 29 wherein said display means comprises means for displaying a perspective representation identifying a motion path of said region and containing the outline of said focus zone.

31. A therapy system as claimed in claim 29 wherein said display means comprises means for generating a two-dimensional image with a third dimension represented by different chromatic values.

32. A therapy system as claimed in claim 29 wherein said display means comprises means for generating a two-dimensional image with a third dimension illustrated by different grayscale values.

33. A therapy system as claimed in claim 29 wherein said display means includes means for graphically emphasizing a current position of said region.

34. A therapy system for administering acoustic energy to a subject respirating at a respiration frequency comprising:
means for generating acoustic waves focused at a focus zone;
means for effecting relative three-dimensional displacement between said focus zone and a subject to be treated with said focused acoustic waves, said subject containing a region to be charged with said focused acoustic waves, said region moving at the respiration frequency; and locating means for non-invasively, repeatedly acquiring a three-dimensional spatial position of said region within said subject at a repetition rate which is at least twenty times higher than the respiration frequency for controlling said means for effecting relative displacement such that said focus zone and said region are in substantial coincidence, at least when charging said region with said focused acoustic waves.

35. A therapy system for administering acoustic energy to a subject comprising: means for generating acoustic waves focused at a focus zone;

means for effecting relative three-dimensional displacement between said focus zone and a subject to be treated with said focused acoustic waves; and locating means for non-invasively acquiring and storing coordinate data along three orthogonal directions for identifying a three-dimensional spatial position of a region to be charged with said focused acoustic waves within said subject continuously as a function of time for controlling said means for effecting relative displacement such that said focus zone and said region are in substantial coincidence, at least when charging said region with said focused acoustic waves.

* * * * *